United States Patent
Piechotta et al.

(10) Patent No.: US 9,482,651 B2
(45) Date of Patent: Nov. 1, 2016

(54) CHIP PRODUCED AT WAFER LEVEL FOR LIQUID CHROMATOGRAPHY AND METHOD FOR THE PRODUCTION THEREOF

(75) Inventors: Gundula Piechotta, Hohenaspe (DE); Hans-Joachim Quenzer, Itzehoe (DE)

(73) Assignee: Fraunhofer-Gesellschaft Zur Foerderung Der Angewandten Forschung E.V., Munich (DE)

( * ) Notice: Subject to any disclaimer, the term of this patent is extended or adjusted under 35 U.S.C. 154(b) by 1180 days.

(21) Appl. No.: 13/508,196
(22) PCT Filed: Nov. 5, 2010
(86) PCT No.: PCT/EP2010/066939
§ 371 (c)(1),
(2), (4) Date: Jul. 16, 2012

(87) PCT Pub. No.: WO2011/054938
PCT Pub. Date: May 12, 2011

(65) Prior Publication Data
US 2012/0273350 A1    Nov. 1, 2012

(30) Foreign Application Priority Data
Nov. 6, 2009   (DE) ........................ 10 2009 052 234

(51) Int. Cl.
G01N 30/56    (2006.01)
G01N 30/60    (2006.01)
G01N 30/52    (2006.01)

(52) U.S. Cl.
CPC ..... *G01N 30/6095* (2013.01); *G01N 2030/528* (2013.01)

(58) Field of Classification Search
CPC .. G01N 30/48; G01N 30/482; G01N 30/484; G01N 30/486; G01N 2030/6056
USPC ........ 422/70, 502–503; 73/61.53; 210/198.2, 210/656
See application file for complete search history.

(56) References Cited

U.S. PATENT DOCUMENTS 6,156,273 A    12/2000  Regnler et al.
7,115,422 B1   10/2006  Gilton
(Continued)

FOREIGN PATENT DOCUMENTS

DE    10 2004 050 569 B3    6/2006
EP        1 319 948 A2       6/2003
(Continued)

OTHER PUBLICATIONS

Blom et al., "On-Chip Hydrodynamic Chromatography Separation and Detection from Nanoparticles and Biomolecules", Analytical Chemistry, Dec. 2003, vol. 75, No. 24, pp. 6761-6768.
(Continued)

*Primary Examiner* — Jan Ludlow
(74) *Attorney, Agent, or Firm* — Dority & Manning, P.A.

(57) ABSTRACT

The present invention relates to a method for producing a miniaturized separation column for chromatographic purposes including a porous stationary phase anchored in the column, including the following steps:
(a) preparing a flat substrate of silicon, glass, glass ceramic or ceramic;
(b) etching at least one channel structure into the flat substrate;
(c) introducing a non-porous precursor material for the porous stationary phase into at least one portion of the channel structure (s);
(d) forming a porous, three-dimensional network from the precursor material; and
(e) fluid-tight covering of the channel structure(s) on the top side of the flat substrate.

7 Claims, 1 Drawing Sheet

(56) References Cited

U.S. PATENT DOCUMENTS

| | | |
|---|---|---|
| 7,217,367 B2 | 5/2007 | Huang et al. |
| 7,314,505 B1 | 1/2008 | Wheeler et al. |
| 2002/0166816 A1 | 11/2002 | Allen et al. |
| 2008/0318334 A1 | 12/2008 | Robotti |
| 2009/0053470 A1 | 2/2009 | Desmet |

FOREIGN PATENT DOCUMENTS

| | | |
|---|---|---|
| EP | 1 319 949 A1 | 6/2003 |
| JP | 2001-343377 A | 12/2001 |
| JP | 2003311008 | 11/2003 |
| WO | WO 92/02951 | 2/1992 |
| WO | WO 01/53819 A1 | 7/2001 |
| WO | WO 2004/010135 | 1/2004 |
| WO | WO 2004/055506 A1 | 7/2004 |

OTHER PUBLICATIONS

Clicq et al., "Porous Silicon as Stationary Phase for Shear-Driven Chromatography", Journal of Chromatography, Apr. 2004, vol. 1032, Nos. 1-2, pp. 185-191.

De Malsche et al., "Integration of Porous Layers in Ordered Pillar Arrays for Liquid Chromatography", Lab on a Chip, Dec. 2007, vol. 7, No. 12, pp. 1705-1711.

De Pra et al., "Pillar-Structured Microchannels for On-Chip Liquid Chromatography: Evaluation of the Permeability and Separation Performance", Journal of Separation Science, Jul. 2007, vol. 30, No. 10, pp. 1453-1460.

He et al., "Ion Liquid Chromatography On-A-Chip with Beads-Packed Parylene Column", Micro Electro Mechanical Systems, 2004, 17th IEEE International Conference, pp. 212-215.

Ishida et al., "Microchip Reversed-Phase Liquid Chromatography with Packed Column and Electrochemical Flow Cell Using Polystrene/poly(diemethylsiloxane", Journal of Chromatography, Dec. 2008, vol. 1213, No. 2, pp. 209-217.

Ishida et al., "Reversed-Phase Liquid Chromatography on a Microchip with Sample injector and Monolithic Silica Column", Journal of Chromatography, Nov. 2006, vol. 1132, Nos. 1-2, pp. 90-98.

Levkin et al., "Monolithic Porous Polymer Stationary Phases in Polyimide Chips for Fast High-Performance Liquid Chromatography separation of Proteins and Peptides", Journal of Chromatography, Jul. 2008, vol. 1200, No. 1, pp. 55-61.

Ocvirk et al., "Integration of a Micro Liquid Chromatography onto a Silicon Chip", Transducers 1995, The 8th International Conference on Solid-State Sensors and Actuators and Eurosensors IX, Stockholm, Sweden, Jun. 25-29, 1995, pp. 756-759.

Puy et al., "Influence of the Hydrothermal Treatment on the Chromatographic Properties of Monolithic Silica Capillaries for Nano-Liquid Chromatography of Capillary Electrochromatography", Journal of Chromatography, Aug. 2007, vol. 1160, Nos. 1-2, pp. 150-159.

Shulga et al., "Preparation and Characterization of Porous Gold and Its Application as a Platform for Immobilization of Acetylcholine Esterase", Chemistry of Materials, 2007, vol. 19, vol. 16, pp. 3902-3911.

Kimura, et al., "High Efficiency HPLC Separation Using Monolithic Silica Columns", 2004.

Nakamura, "Knack for Liquid Chromatography a Little in Detail", 2007.

Wu, et al., "Microchip-Bases Macroporous Silica Sol-Gel Monolith for Efficient Isolation of DNA from Clinical Samples", Analytical Chemistry, vol. 78, pp. 5704-5710; Aug. 15, 2006.

CHIP PRODUCED AT WAFER LEVEL FOR LIQUID CHROMATOGRAPHY AND METHOD FOR THE PRODUCTION THEREOF

This application is a national stage entry of PCT/EP2010/066939, filed Nov. 5, 2010.

The present invention relates to miniaturized separation columns for chromatographic purposes, for example, "on-chip liquid chromatography," that are produced by the etching out of channels, respectively of recesses in a substrate, filling of the recesses with a monolithic precursor of the later stationary phase and—subsequently to the formation of pores in the stationary phase—sealingly covering the channel structures formed. The separation columns that are obtainable using these method steps have a self-supporting three-dimensional structure that is fixedly anchored to the substrate wall and is filled with a porous stationary phase, and whose lateral walls are partially formed by the substrate and partially by the covering.

The present invention may be advantageously realized using flat substrates which are available in the form of chips or wafers and can be processed, in particular etched, using micromechanical method steps.

The liquid chromatographic separation of molecules and, more specifically in this connection, high-pressure liquid chromatography (HPLC) is the method most frequently used in chemical and biochemical analytics. The analyses are generally performed in large automated laboratory systems equipped with separation columns, usually having dimensions of 10-20 cm in length and of 10 mm inside diameter. Chip-based miniaturization approaches, which have the advantages of low sample consumption and split-second separation performance, are generally described in the literature. Until now, however, no separation column has been described that is capable of achieving satisfactory and reproducible separation performances.

Chip-based miniaturization approaches for liquid-chromatographic applications are mostly described in the literature with reference to silicon and/or glass chips. Different approaches have been taken for realizing a separation column composed of a capillary or of an etched recess and of a porous stationary phase possibly contained therein. The various approaches described are presented exemplarily in the following:

In *On-chip hydrodynamic chromatography separation and detection of nanoparticles and biomolecules*, Anal. Chem. 2003, 75, 6761-6768, Blom, M. T., Chmela E., Oosterbroek R. E., Tijssen R., and Van den Berg A. describe a planar separation channel that does not have a stationary phase. It relates to a channel used for a molecule separation process based on hydrodynamic chromatography at an operating pressure of 3.5 bar and having a channel height of 1 µm and a channel width of 0.5/1 mm. Interconnected channels in monolithic support structures are known from U.S. Pat. No. 6,156,273, Separation columns and methods for manufacturing the improved separation columns.

In *Pillar-structured microchannels for on-chip liquid chromatography: Evaluation of the permeability and separation performance*, J. Sep. Sci. 2007, 30, 1453-1460, De Pra M., De Malsche W., Desmet G., Schoenmakers P. J., and Kok W. Th. describe channels have 2D-etched structures (pillars). A channel having pillars is formed in a silicon chip by high-rate etching; the channel is 50 µm wide and 100 µm deep. Various pillar geometries and inter-pillar spacings are described. The pillar height is 10 µm; the pillar width is +/−5 µm. A porous outer layer of 200 nm on etched pillars (19/5 µm) is known from De Malsche W., Clicq D., Verdoold V., Gzil P., Desmet G., Gardeniers H.: *Integration of porous layers in ordered pillar arrays for liquid chromatography*, Lab Chip 2007, 7, 1705-1711. It is produced by additionally anodically etching the outer pillar walls in order to increase the surface area of the separation layer. In the chromatography columns of U.S. Pat. No. 7,217,367 B2, pillars coated with the material of the stationary phase can be used. They are suited for OTLC (open tubular liquid chromatography) or PCLC (packed column chromatography systems) or combinations thereof.

U.S. Pat. No. 7,115,422 B1 describes silicon chips having porously etched capillary separation channels. In *Porous silicon as stationary phase for shear-driven chromatography*, J. Chromatogr. 2004, 1032, 185-191, Clicq D., Tjerkstra R. W., Gardeniers J. G. E., Van den Berg A., Baron G. V., and Desmet G. present channels of porously etched silicon. They are silicon chips having parallel disposed channels; the channel dimensions are: 100-500 nm depth, 750 µm width. The channels are first produced by etching through an $SiO_2$ mask in the usual manner; a porous silicon layer is subsequently formed on the channel floor by anodic HF etching. A silicon dioxide surface is then likely to form by later contact with water. It can ultimately be organically functionalized with dimethyloctylchlorosilane.

Gas chromatography requires capillary separation columns that are coated with a few molecule layers. The European Patent Application EP 1 319 949 A2 discusses this type of chromatography column that is formed from two interconnected glass substrates, of which one has an etched-in channel. The etched-in channel walls of the first substrate are provided with a coating from a stationary phase, and, in fact, by the successive loading of suitable chemicals in each instance and evaporation of the solvent. An alkyl coating having a thickness of more than 60 silicon atoms can be thereby obtained in six steps. The channel is subsequently closed by placement of the second glass substrate thereon. U.S. Pat. No. 7,314,505 B1 likewise describes coating the channel walls with a stationary phase. Onium salts, which have a functional group Z, are used for binding the molecules of this phase. A polysiloxane or a polyethylene glycol is bound thereto. Given a vinylated PDMS coating, the total layer thickness was approximately 4 µm. The German Patent Application DE 10 2004 050 569 B3 discusses using an adhesion promoter to produce a coated GC separation column. In principle, however, separation columns, whose stationary phase does not extend through the entire or, at least, not nearly through the entire cross section of the column, are not suited for many liquid chromatography applications.

In *Ion liquid chromatography on-a-chip with bead-packed parylene column*, IEEE 2004, 0-7803-8265-X, He Q., Pang C., Tai Y.-C., Lee T. D. describe separation columns packed with particles. The columns contain micro-beads (7 µm PS-DVB beads) between frits. The bottom sides of the columns are made of silicon; the top sides of parylene. The attainable operating pressure is between 250-800 psi. The height of the columns is 25 µm. In *Integration of a micro liquid chromatograph onto a silicon chip*, Transducers 1995, the 8th International Conference on Solid-State Sensors and Actuators, and Eurosensors IX, Stockholm, Sweden, Jun. 25-29, 1995, Ocvirk G., Verpoorte E., Manz A., Widmer H. M. discuss micro-beads (3-5 µm) between Si/glass-Si having frits. The column is 300 µm wide, 100 µm deep and 20 mm long. A split injector and the optical detection devices are integrated on the chip.

In Journal of Chromatography A, 1213 (2008) 209-217, Ishida A., Natsume M., Kamidate T. describe a microchip of polystyrene having a mechanically introduced bore as a columnar channel. With the aid of Au deposition and etchings, an electrode system used for amperometric detection is mounted on the surface of the polystyrene substrate. Channel structures were produced with the aid of polydimethylsiloxane (PDMS). Spherical C18 silicon dioxide particles were used as the stationary phase.

In *Reversed-phase liquid chromatography on a microchip with sample injector and monolithic silica column*, J. Chromatogr. A 2006, 1132, 90-98, the work group led by A. Ishida (see Ishida A., Yoshikawa T., Natsume M., Kamidate T.) describes monolithically produced 3D structures of glass/Pyrex. The etched channels have a serpentine structure having narrowed curves, a channel width of 400 μm, a channel depth of 30 μm, and a channel length of 42 cm. The channels are filled with a porous stationary phase of organically modified silicon dioxide particles that were produced by the introduction of a tetramethoxysilane sol, subsequent heating, drying and modification of the formed silicon dioxide with octadecyl trichlorsilane.

In *Influence of the hydrothermal treatment on the chromatographic properties of monolithic silica capillaries for nano-liquid chromatography or capillary electrochromatography*, J. Chromatogr. A 2007, 1160, 150-159, Puy G., Roux, R., Demesmay C., Rocca J.-L., Iapichella J., Galarneau A., Brunel D. describe the production of glass capillaries (capillaries of "fused silica") filled with modified silicon dioxide. The empty capillaries were activated with sodium hydroxide solution. Following elution, they were filled with a mixture of polyethylene glycol (PEG), urea, acetic acid and tetramethoxysilane. The capillaries were sealed and the contents subjected to aging to bring about gelation. Heating the sealed capillaries (hydrothermal treatment) then produced mesopores in the filling in a targeted manner, the urea being thereby hydrolyzed to ammonia. Lastly, the PEG was eluted. In an alternative approach, the silicon dioxide was modified in the capillaries using octyl chains. The hydrothermal treatment proved to be necessary only for the octyl-modified silicon dioxide; without this treatment, the efficiency decreased here by a factor of 2.

In *Monolithic porous polymer stationary phases in polyimide chips for the fast high-performance liquid chromatography separation of proteins and peptides*, J. Chromatogr. 2008, 1200, 55-61, Levkin P. A., Eeltink S., Stratton T. R., Brennen R., Robotti K., Yin H., Killeen K., Svec, F., Frechet J. M. J. describe stationary phases from a poly(lauryl methacrylate-co-ethylene dimethacrylate) or poly(styrene-co-divinylbenzene) in polyimide chip channels, which have dimensions of 200 μm×200 μm×6.8 cm. The stationary phases are produced monolithically, in the presence of porogenene(1,4-butandiol or 1-propanol for the methacrylate phase, 1-decanol or THF for the styrene-divinylbenzene phase), which were then eluted with methanol.

U.S. Patent Application 2002/0166816 discusses a chromatography device and methods that can be carried out using the same, that are implemented using a disposable cartridge, whose channels are filled flexibly and with a monolithic stationary phase. The phase may be made up of organic, polymer or inorganic material. Silicon dioxide-based materials are mentioned as an example of the latter. The specification discusses producing the monolithic phase within the channel; alternatively, the monolith can be prefabricated and then introduced into the channel. This publication does not incorporate a technical teaching for producing the monolith.

Inherent in the methods discussed above are one or more of the following disadvantages:

Most of the columns described must be filled individually at the chip level. It is mechanically difficult to introduce a separate, porous stationary phase into the microchannels, particularly when the channels are only accessible at the ends; the use of spray applications or the like is then inevitable; also unavoidable are irregularities in the distribution of the stationary phase in the channel. Reliable measurements are, therefore, impossible.

Stationary phases in the form of particles can only be packed into finished columns. The three-dimensional matrix is dependent on the packing density. Due to the small column geometries, the particles can only be packed into miniaturized columns at a high density with great difficulty and minimal reproducibility. The process is very drawn-out and is typically performed manually for each chip, since the difficult accessibility makes an automation hardly possible for a plurality of columns. This is also incompatible with a reliable, reproducible chromatography.

There are some related art approaches for producing monolithic precursors of the later stationary phases and of subsequently providing them with pores. However, these are introduced in all cases into already prefabricated columns, so that the mechanical difficulties mentioned above occur again during filling. During curing of the (still monolithic) stationary phases and upon removal of the particular solvent, changes in the three-dimensional matrix, such as contraction or [the emergence of] pores that are unplanned and uncontrolled in terms of the size thereof, can occur due to surface tensions and other effects. A permanent binding of the stationary phases to the column walls is likewise typically not reached.

Only in the case of subsequently oxidized silicon as a stationary phase etched out of the substrate, has it been possible under known methods heretofore to form this phase monolithically and so as to be stably anchored chemically, respectively mechanically to the channels. However, with the aid of anodic etching, it is possible to achieve only a very small depth of the "channel;" the aspect ratio is too small; one obtains only a very narrow band as a separation channel. Thus, variations in the column geometry are not possible. It is possible that, for this reason, U.S. Pat. No. 7,115,422 B1 most notably emphasizes separation channels that do not have any appreciable porous stationary phase at all, rather a channel surface that is composed of roughened silicon. Moreover, when a stationary phase is etched out of a silicon substrate by anodic etching, the surface of this phase is often excessively etched as well, so that it no longer terminates flush with the substrate surface; the gap formed makes the covering problematic. Therefore, the question of a sealing surface is possibly completely excluded from consideration in U.S. Pat. No. 7,115,422 B1. Finally, the pore surface obtained by etching is unsatisfactorily small.

It is an object of the present invention to provide a remedy therefor and to devise a method that will make it possible to rapidly produce a plurality of reliably and reproducibly functioning miniaturized chromatography columns at the wafer level that are filled with a stationary phase at least in one portion of the column over the entire cross section thereof.

To achieve the objective, a method is provided for manufacturing a miniaturized separation column containing a porous stationary phase, encompassing the steps of:

(a) preparing a flat substrate of silicon, glass, ceramic or glass ceramic;

(b) etching one or a plurality of (horizontal) channel structures into the flat substrate;
(c) introducing a non-porous precursor material for the stationary phase into at least one portion of the channel structure(s);
(d) forming a porous, three-dimensional network from the precursor material; and
(e) fluid-tight covering of the channel structures on the top side of the flat substrate.

Figure 1:
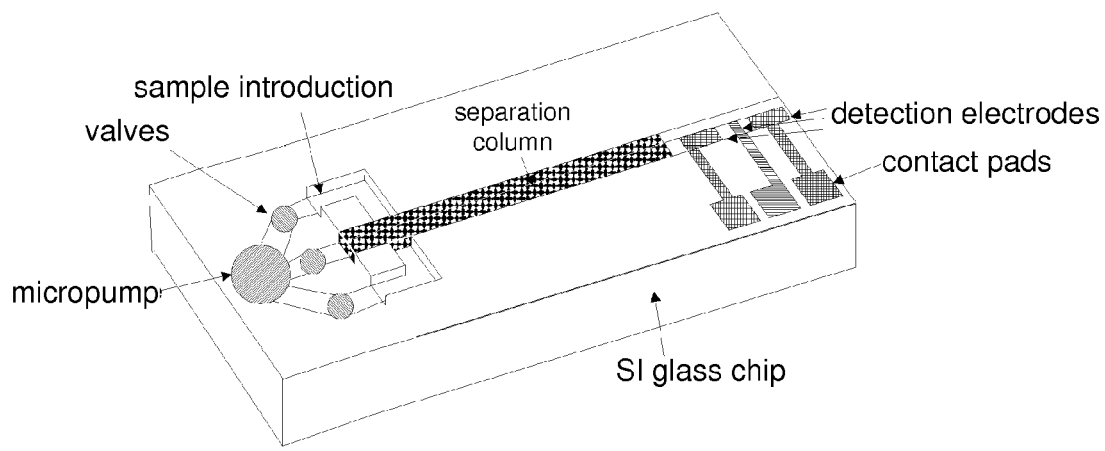
FIG. 1 shows a chip of the instant invention.

The method according to the present invention makes it possible to provide miniaturized "chromatography chips" suited for chromatography purposes, each having one or a plurality of separation channels that are embedded in any given form in the substrate of the chip and are filled with a porous ("monolithic") stationary phase that forms a three-dimensional network and that permanently adheres, chemically or mechanically, to the at least one portion of the channel wall. The phase is composed of an inorganic or of an organically modified inorganic material, selected from among metals, ceramics and, in some instances, metal or semi-metal compounds that may be all-organic or surface-modified (as semimetal, silicon should be mentioned here, in particular, as a semimetal compound, in some instances organically modified silicic acid polycondensates, in whose Si—O—Si matrix, heteroatoms, for instance metal atoms, can be inserted). In individual cases, the phase may also be composed of a purely organic material, provided that it is either able to for m a sufficient chemical bond with free SiOH groups on the substrate surface, or provided that the surface of the separation channel wall is organically modified (for example, by a silanization) in a way that allows a sufficient chemical bond to form between the organic groups of the channel wall surface and those of the stationary phase, thereby achieving the requisite mechanical stability.

As an individual channel, each separation channel may reside in any given configuration (extending in the straight form length of the substrate, coiled, zigzag, spiral-shaped or the like) on the substrate that forms the chip; however, a plurality of such separation channels may also reside on one chip. A plurality of columns are preferably formed on a wafer substrate that is later diced into separate chips, each having one or more columns.

Suited as a substrate are all materials, whose surface contains SiOH groups or is able to form the same in humid air or other suitable environment, i.e., silicon, glass, ceramics, as well as glass ceramics, in particular in the form of wafers that may be subsequently diced. In some instances, the substrate surface may be organically modified by Si—O groups, for example, by reaction with silanes of the formula $R^1_a R^2_b SiX_{4-a-b}$, $R^1$ being a residue bound via carbon to the silicon having the properties required for binding to an organic stationary phase (for example, including a carboxylic acid group for an ester bond or a double bond that may be polymerized thermally or in a different manner together with comparable double bonds of the organic material of the later stationary phase), $R^2$ representing any given other, mostly organic residue, for example, an alkyl residue, X OH or a leaving group that renders possible a hydrolytic condensation leading to the formation of Si—O—Si bridges; a being equal to 1, 2 or 3, b being equal to 0, 1 or 2, and a+b being maximally 3. X may be an alkoxide, chloride or one of the other groups known from the related art.

The separation channels are formed as recesses in the substrate in such a way that the substrate at least forms the (rear) lateral wall and a portion of or all of the lateral walls contiguous thereto, while a last portion of the lateral wall of the separation channels is formed later, following introduction of the stationary phase, by a cover extending in the longitudinal direction of the later column. Producing such recesses is known from the related art. Suited for this are mechanical methods, in particular etching methods, however. The recesses may be produced in a known manner using what is generally referred to as MEMS technology, i.e., at the wafer level using conventional methods for manufacturing micromechanical/microelectronic components. These include the etching of silicon or glass substrates using lithography, in particular, using stationary (for example, oxidic) or applied masks. The dimensions of the separation columns may be selected in any desired manner in accordance with the particular requirements; they frequently have a width of approximately 1-1000 µm, preferably approximately 1-500 µm, a height of approximately 1-1000 µm, preferably approximately 1-500 µm (respectively, a cross section of approximately 1-1000 µm², preferably approximately 1-500 µm²) and a length of approximately 0.1, preferably 1 to 100 mm. They may have any given cross section, for example, round, oval, trapezoidal or square.

The recesses, respectively channels are then filled with a material that is a precursor material of the later stationary phase which is to be used in the chromatographic method that is applied in each instance. The precursor material is subsequently treated in a way that allows it to form the mentioned stationary phase. It should be inherently stable, i.e., have a three-dimensional matrix structure that is permanently anchored in the column wall (preferably chemically and/or physically, for example, on the basis of physical adsorption). Such a matrix structure is also referred to as "monolith" (see FIG. 2A). A stationary phase having an inherently stable matrix structure differs from the particulate stationary phases in that it features self-supporting properties and the form thereof would, therefore, be retained if one were able to release it undamaged from the column and store it.

For this purpose, the channels are filled up to a predetermined height with a precursor material for the porous phase that adheres to the channel walls. When the conversion of the precursor material into the porous phase does not pose any risk of changes in volume, the fill height of the precursor material is preferably level with the substrate surface. Otherwise (for instance, in the case of an expected slight contraction of the material), a slight excess length may be provided that may be stabilized by suitable surface properties (hydrophilicity, hydrophobicity) of the substrate or of the precursor material in a way that prevents any gap from forming once the material is converted into the porous stationary phase, even when the channel cover is to be in the form of a rigid plate. However, this precautionary measure is only necessary in exceptional cases, since it is preferred to provide a conformal cover.

There is no need for the channels to be completely filled in the longitudinal extension. It may be beneficial to keep the channel regions contiguous to the inlet and outlet orifices free of the stationary phase. Viewed in cross section, at least one portion of the channels should be completely or essentially filled with the porous phase.

Once the channels are filled, the material is provided with the desired pores (see FIG. 2A).

In a first embodiment of the present invention, the material for the stationary phase may be a metal. In accordance with the present invention, "metal" is to be understood as a true metal, i.e., not a semimetal such as silicon. The metal is intimately bonded to the channel wall, for example, with the aid of a previous activation of the channel wall material. This may be a question of a corona pretreatment or of a light etching. Instead, or additionally thereto, a primer layer may be deposited. In some instances, a starting layer (seed layer) is deposited from the same or from another suitable metal, to render possible an electrodeposition of the metal intended for the stationary phase, for instance by vapor deposition. Examples of metal depositions are those of gold, gold-platinum alloys or other gold-containing alloys. As a chromatographic material, gold is suited, in particular, for the present invention because gold surfaces may enter into thiol couplings. Via this reaction, hydrophilic or hydrophobic organic groups may be attached to the gold surface that are tailored to the particular desired chromatographic processes, respectively that define the desired separation properties of the resulting column. An example of this is modification using $C_8$ or $C_{18}$ carbon atoms which effect a hydrophobization of the stationary phase. Such hydrophobic, respectively hydrophobized phases are utilized for "reversed-phase" chromatography. In some instances, sulfide-containing molecules may also be captured by gold surfaces, or the separation channels are used for the chromatographic processes that utilize capture molecules that may be bound via SH bonds ("self assembling") to the gold framework.

To produce a porous, monolithic gold phase, a gold alloy having a less noble metal is preferably deposited in the channel, whereupon the non-noble metal is eluted from the alloy by oxidation, for example using a strong acid, such as nitric acid. Such a method is known, for example, from O. V. Shulga et al., *Preparation and Characterization of Porous Gold and Its Application as a Platform for Immobilization of Acetylcholine Esterase* in Chem. Mater. 2007, 19, 3903-3911. However, a porous gold phase may also be produced in the channel in another way, for example, by the thermal decomposition of gold oxide ($Au_2O_3$), the sublimation of iodine from $AuI_2$ powder, the electrochemical treatment of polycrystalline gold or the dissolution of gold chloride in a suitable solution, for example, a dextran solution, and the heating of this solution to 600-800° C., in order to remove the organic portions and to effect a reduction and, in the process, sintering of the gold following removal of the solvent. These methods are also known from O. V. Shulga, a.a.O.

Besides gold, other metals, such as platinum or aluminum, may be used to the extent that these metals may be desired for specific purposes. If aluminum is used, the stationary phase may be composed of aluminum oxide to any given depth, and, besides oxygen atoms, the surface thereof may bear hydroxyl groups. Independently of this specific embodiment, the stationary phase may also be produced from mixtures of gold or of another metal/of an alloy having another metallic or non-metallic material in such a way that one of the two materials forms the stationary phase in the form of a matrix in which the other material is embedded (see FIG. 2C). The other metallic or non-metallic material may likewise be provided for chromatographic tasks, for example, effect other retention times or the retention of other molecules. Instead, or additionally thereto, it may fulfill other tasks, for instance, have a different (for example, lower) electrical conductivity than the gold or other metal/the mentioned alloy. Alternatively, stratifications (lengthwise with respect to the channel or transversely thereto) of two or more materials are possible, as mentioned above. In the last-mentioned embodiment, the geometry and the materials may be selected in a way that provides an electrical contacting in each case at the contact point of one of the materials with the silicon of the substrate via which information, pertaining, for example, to the loading of this material may be tapped off (see FIG. 2B). For example, an optionally organically modified silicon dioxide may be used as another material; however, air may also be used for this.

The gold, respectively each gold compartment may feature one or a plurality of electrical contact leads. A potential may be applied to the gold, enabling the separation column to be utilized for electrical movement (electrophoresis) or for detecting molecules.

In another embodiment of the present invention, the material for the stationary phase may be a (ceramic or non-ceramic) oxide. Besides metal oxides of the main group metals and transition metals, silicon oxides are suited here, in particular, which may be organically modified, or porously etched glass.

If a silicon oxide is provided, it should be noted that it was produced using a method that has a monolithic structure as a reliable result. Thus, xerogels are not suited, for example, while the aerogels are monolithic oxide structures, which may be readily used for the present invention. These may be produced, for example, in that a liquid $SiO_2$ phase in a suitable solvent is introduced into the etched separation channel(s) and is solidified by supercritical drying using $CO_2$. By evaporating the solvent using the supercritical drying process, a separation column structure having a very large surface area is obtained that features a plurality of gas inclusions and branches in a spongelike form. In subsequent steps, the $SiO_2$ surface may be modified/functionalized by depositing organic layers in a way that enables the column to fulfill the desired separation tasks. An example of this, in turn, is the modification by C8 or C18 carbon chains for reversed phase HPLC, as described above for gold as a stationary phase; in this case, the modification is preferably effected by a silanization, as known from the related art.

Ceramic/metal oxides do not necessarily need to be constituted of silicon oxide or contain the same. Another example of an, in particular ceramic, oxide is porous aluminum oxide, for example, that is produced by galvanic deposition or electroless plating of aluminum and the subsequent, in particular anodic, etching using hydrochloric acid, sulfuric acid or nitric acid to produce pores. In many cases, the core of such stationary phases may also contain aluminum metal. Implementing the process, aluminum oxide is obtained as a pore/column matrix that represents a desired surface for a plurality of separation tasks.

Porous glass is obtained, for example, using what is generally referred to as the Vycor process. Introduced into channels located in the substrate is a glass, which may separate from a homogeneous mass into two glass phases, of which one is a glass having predominantly siliceous structures, and the other is a glass having predominantly borate-containing structures (Vycor glass). As a function of the original glass composition and the temperature used for the separation, a stationary phase composed of two interpenetrating networks of the two glass phases forms in the channels. By selectively etching out the one (here, in particular of the borate-containing) phase, a porous structure is obtained that is predominantly composed of $SiO_2$. As described above with respect to the aerogel, this porous structure may also be organically modified/functionalized.

Organic polymers may also be used in accordance with the present invention as a monolithic phase. Thus, analogously to the Vycor process, a liquid polymer mixture, that is composed of at least two different hydrophilic/hydrophobic polymers or polymer precursors, as well as possibly an emulsifying agent and/or other auxiliary agents, may also be introduced into the channel(s). Through curing (polymerization/cross-linking, respectively post-cross-linking), for example, by raising the temperature, by UV irradiation, or in some other way, two interpenetrating networks of the various polymers form, of which one may be eluted by selecting a suitable solvent in which only this polymer dissolves. Subsequently to this process, the porous plastic matrix may be functionalized by binding hydrophilic or hydrophobic groups to the surface reactive groups of the polymer. It is intended in this specific embodiment that the channel walls be preferably modified by organic groups in a way that allows the portion of the polymer forming the stationary phase and remaining following elution to be anchored thereto by chemical bonds.

Following the formation of the porous stationary phase in the channel(s) of the individual substrate or of the wafer, the filled channels are appropriately covered or sealed. This may be accomplished by a conformal deposition, i.e., a deposition that is closely adapted to the surface of the channel, but is not pore-filling, of one or a plurality of materials on the channels, optionally also on the entire substrate surface. Depositions from the gas phase or galvanic processes may be advantageously used; suited as deposition techniques are, for example, CVD or PECVD (chemical vapor deposition or plasma enhanced chemical vapor deposition), but also sputtering techniques. Suited as materials are nitrides or oxides, mainly of silicon, however, also, for example, of aluminum, gallium or other metal cations, in addition, parylenes or metals, such as gold, platinum, iridium, silver and others. When necessary, the cover may be structured later, for example, provided with holes or recesses. Further depositions may follow in order to apply metallizations, contacts or the like. The conformal deposition has the advantage of allowing the stationary phase of the chromatography column according to the present invention to generally be chemically or physically bound to all channel walls surrounding them.

A covering may also be effected, however, by covering the chips/the wafers with a plate of glass, silicon or plastic via anodic bonding, adhesive bonding or by another method that permanently bonds two components, it being necessary in most cases for the covering to be effected so as to be airtight at least in the area of the separation column, and for it to be able to feature still further structurization, for example, holes, recesses, metallization, contacts or the like over the entire surface, top and bottom.

If indicated, the covering or sealing of the channels may be effected prior to modification of the stationary phase, as described above, because such a modification may be carried out, inter alia, with the aid of a solution that is pumped through the closed channel. Alternatively, however, the modification may also be undertaken before the channels are covered.

The etching of the channels, the introduction of the precursor material for the stationary phase, the formation of the porous stationary phase, as well as the covering of the channels may take place on one single chip (substrate) or, however, at the wafer level. In the latter case, a plurality of channels, provided in each case for one single subsequent chip, are etched onto the wafer, filled and sealed; the wafer is subsequently diced into separate pieces. In this context, the singularized wafer substrate may serve as a chip substrate; alternatively, it is adhesively bonded to another substrate or deposited using other methods. The particular substrate may then feature or accommodate, for example, the or a portion of the units that are described in the following in the context of the substrate featuring the channel(s).

One or more sample introduction units, one or more micropumps, microvalves and/or one or a plurality of electrodes used for electrochemical detection, for example, for pulsed voltammetry, impedance or others may be integrated on the liquid chromatography chip. Such units may also be either mounted individually on the individual chips (i.e., on the substrate containing the channel(s), or on a different substrate (see the preceding paragraph); or they (or some of them) are produced using wafer technology on the substrate (for example, by metallizations, etchings or the like), and, following the singularization, reside, together with the channel structures, on a substrate provided for the same chip. Alternatively, the units mentioned, or a portion thereof, may be externally present and be bonded to the chip for the chromatography process.

Devices and contacts for tempering the separation columns or the entire chip and/or a temperature sensor may be optionally provided on the chromatography chip. Moreover, the technical prerequisites (valves, pump(s), supply lines and a programming) required for sending solvent gradients across the separation column may be integrated. For the manufacturing, respectively configuration of these components, the same holds as for the aforementioned sample introduction units, micropumps, microvalves and electrodes.

The above mentioned materials and the manufacturing processes provide a high level of ruggedness and reproducibility of the chips described for the liquid chromatographic separations and identifications of a broad array of chemical and biochemical molecules. This eliminates the need for a complex and costly packing of the columns that can result in poor reproducibility and separation efficiencies. The miniaturization at the chip level makes it possible to extend liquid chromatography into the realm of portable and flexible on-site analytics. Only a few seconds will be required for separation and analysis.

The materials provided in the approach according to the present invention feature a myriad of advantageous properties for liquid chromatographic applications.

Substantial mechanical stability, that is vitally important for high-pressure liquid chromatography in particular;

Silicon dioxide is a standard column material, so that, in this case, all existing coating/functionalization materials for classic columns may be used;

Aluminum dioxide is likewise a standard material for a multitude of separations;

Gold has the advantage of optionally allowing a potential to be applied as well, and the column to be utilized for electrical motion or detection of molecules;

a large surface bandwidth may be adjusted from hydrophilic to hydrophobic, enabling a very large analyte spectrum to be processed;

All processes are compatible with Si technology (⅝ inch wafer level), i.e., inexpensive and reproducible production for a large volume.

Liquid chromatographic separations count among the methods most frequently used in chemical and biochemical analytics. A virtually unlimited field of application is opened up by using the described methods for integrating the stationary phase/separation column into a chip for miniaturizing chromatography and for realizing on-chip chromatography. These include, for example, applications in foodstuff analytics and on-site analytics (for instance, antibiotics in milk, mycotoxins in fruits and grains, food ingredients, additives, hormones, pharmacological substances, allergens, general incoming quality inspection, etc.). Other fields of application include, for example, the detection of explosive materials or narcotics, as well as purification and analytics in the biochemistry of peptides, nucleotides, proteins, in particular when only small and/or costly sample quantities are available.

The present invention is explained in greater detail in the following with reference to exemplary embodiments.

EXAMPLE 1

Production of an Aerogel as a Stationary Phase

A viscous solution, prepared in the following manner, was applied by a doctor blade into the etched or sawed recess of a silicon wafer:

1 ml TEOS (tetraethoxysilane), 5 ml ethanol (99%) and 3.5 ml 0.01 M oxalic acid are pipetted into a beaker. The glass is covered with Parafilm, and the mixture is stirred for 24 h at room temperature on the magnetic stirrer. 3.5 ml of 0.5 M ammonia solution are then added; the mixture (covered with Parafilm) is stirred for another 3 h at 45° C. on the magnetic stirrer and then allowed to stand 24 h at room temperature.

Following introduction into the recess, the viscous solution was allowed to gel further for another 24 h at room temperature in the closed wafer container. The wafer was subsequently placed in a device for supercritical drying (Automegasamdri of the firm Tousimis). The purge time for the $CO_2$ was 45 min.

EXAMPLE 2

Production of an Aerogel as a Stationary Phase 1 ml TMOS (tetramethoxysilane), 0.5 ml methanol, 1 ml oxalic acid (0.001 M) are introduced into a sealable plastic vessel (5 ml tube) and slowly swirled for 30 min. at room temperature (hydrolysis of the TMOS). 0.5 ml ammonia solution (0.5 M) are then added.

To avoid air bubbles, the solution is carefully stirred and subsequently poured into the separation-channel recess(es) of a wafer. It is allowed to gel for approximately 30 min. and completely cure for a further 48 h at room temperature. During this time, it must be ensured by air-tight covering that the gel surface does not dry out.

The gel is coated with acetone (at least 10 times the volume of the gel) in order to replace the water/methanol mixture in the gel with acetone (diffusion process) The excess acetone is freshly replaced after approximately 5 h in each case at least three times in order to achieve a complete solvent exchange.

For the final process of manufacturing the separation columns, the (volume-conserving) drying of the gel is carried out via supercritical $CO_2$. For this, the wafer is placed in the "critical point dryer" (Automegasamdri-915B (CPD MEMS Dryer) of the firm Tousimis) where it undergoes the drying program thereof ($CO_2$ purge time: 45 min.).

EXAMPLE 3

Porous Gold as a Stationary Phase

A silicon wafer was lithographically structured, creating channels and contact surfaces. The structuring is carried out in combination with high-rate etching (results in straight etching edges) or wet etching (anisotropic=oblique etching edges) of the silicon wafer with KOH (30% potassium hydroxide solution at 80° C.), respectively TMAH (25% tetramethylammonium hydroxide at 80° C.). The channel bottom and the contacting surface were subsequently vapor-deposited with a galvanic starting layer (gold).

For the contacting of the gold plane, the contacted wafer was placed as a cathode and, a platinized electrode, as an anode, into an electrolyte that is heated to 50° C. and stirred, and is composed, for example, of a 0.15 mol/l gold sulfite, 0.06 mol/l palladium sulfite and 0.5 mol/l sodium sulfite and having a current density of 0.4-0.5 $A/dm^2$ for the deposition of the gold palladium alloy.

Instead of palladium, silver sulfite, copper sulfite, nickel sulfite, zinc sulfite, arsenic sulfite, bismuth sulfite or other base-metal sulfites may be provided for galvanic deposition. Instead of sulfite ions, the metals may also be used with cyanides as anions.

The current densities used for the deposition of the gold are selected as a function of the selected starting materials. They are generally within the range of between approximately 0.05-1 $A/dm^2$ in the case of direct or pulsating current.

It is possible to add auxiliary agents such as EDTA or ethylenediamine, etc.

50% nitric acid solution is used to etch the non-noble metal out of the deposited layer. The time duration is a function of the layer thickness and the percentage of non-noble metal and is generally approximately between 10 and 48 hours.

EXAMPLE 4

Covering the Substrate Following Formation of the Stationary Phase

The wafers treated in accordance with Examples 1 through 3 are introduced into a PECVD oven. A 2 μm thick silicon nitride layer is deposited at 250-450° C. It covers the entire wafer surfaces and thus closes the channel in a conformal and liquid tight manner.

TRANSLATION KEY TO FIGURES

Figure 2:
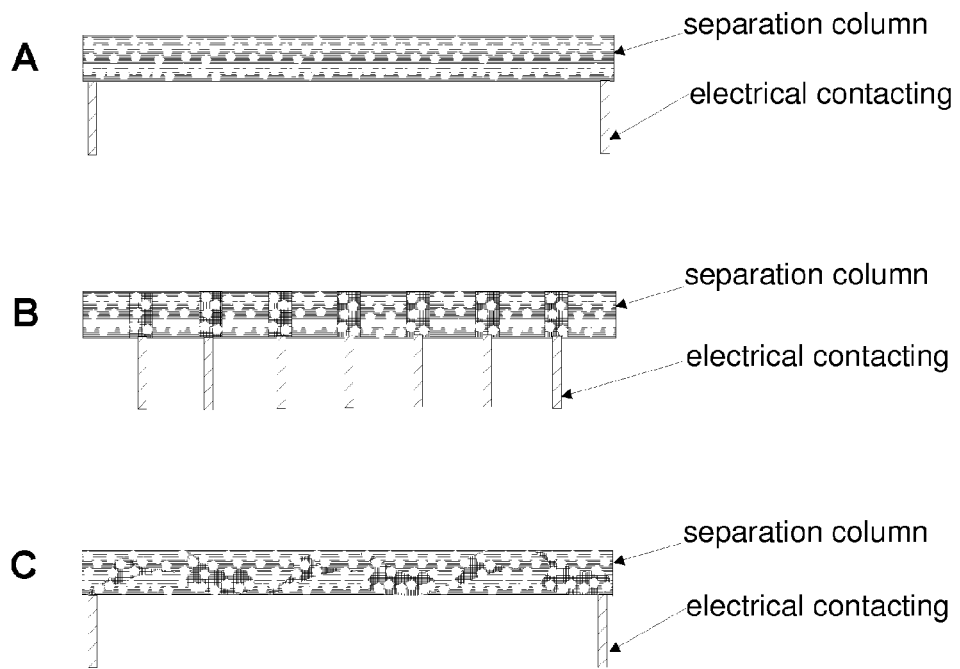
FIGS. 2A-C show a method of making a chip of the instant invention.

FIG. 1
micropump
valves
sample introduction
separation column
detection electrodes
contact pads
SI glass chip
FIG. 2
A
separation column
electrical contacting
B
separation column
electrical contacting
C
separation column
electrical contacting

The invention claimed is:

1. A method for producing a miniaturized separation column for chromatographic purposes including a porous stationary phase anchored in the column, comprising the following steps:
   (a) providing a flat substrate of silicon, glass, glass ceramic or ceramic;
   (b) etching at least one channel structure into the flat substrate;
   (c) introducing a non-porous precursor material for the porous stationary phase into at least one portion of the channel structure(s);
   (d) forming a monolithic, porous, three-dimensional network from the precursor material, wherein when the monolithic, three-dimensional network consists of $SiO_2$, the preparation of this network is made by solidification of a $SiO_2$ solution under maintaining its volume by supercritical drying with $CO_2$;
   (e) liquid tight covering of the channel structure(s) on the top side of the flat substrate by conformal deposition taking place from the gas phase.

2. The method as recited in claim 1, wherein the non-porous precursor material is introduced into the channel structure(s) in such a way that the porous stationary phase after its formation binds chemically thereto or adheres physically thereto.

3. The method as recited in claim 1, wherein the flat substrate is a wafer, and a plurality of channel structures are etched into this substrate.

4. The method as recited in claim 3, wherein the wafer, subsequently to the liquid-tight covering in accordance with step (e) is divided, in particular sawed, into individual components or chips.

5. The method as recited in claim 1, wherein the nonporous precursor material is selected from among metals, in particular gold or aluminum, oxides, in particular silicon dioxide or aluminum oxide, and glass.

6. The method as recited in claim 1, wherein the porous three-dimensional network is modified by organic groups.

7. The method as recited in claim 6, wherein the modification takes place prior or subsequently to the covering of the channel structure(s).

* * * * *